(12) United States Patent
Debenham et al.

(10) Patent No.: US 6,635,784 B2
(45) Date of Patent: Oct. 21, 2003

(54) PROCESS FOR THE PREPARATION OF ENANTIOMERICALLY-ENRICHED CYCLOPROPYLALANINE DERIVATES

(75) Inventors: Sheryl Davis Debenham, Scotch Plains, NJ (US); Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/957,549

(22) Filed: Sep. 20, 2001

(65) Prior Publication Data

US 2002/0049331 A1 Apr. 25, 2002

Related U.S. Application Data

(60) Provisional application No. 60/236,544, filed on Sep. 29, 2000.

(51) Int. Cl.$^7$ .......................... C07C 69/74; C07C 61/04
(52) U.S. Cl. ........................................ 560/124; 562/506
(58) Field of Search ........................... 560/124; 562/506

(56) References Cited

U.S. PATENT DOCUMENTS 4,124,533 A * 11/1978 Knowles et al.
4,414,404 A   11/1983 Roper

FOREIGN PATENT DOCUMENTS

| DE | 199 18 420 | 10/2000 |
| GB | 2266888 | 11/1993 |
| JP | 8-73400 | 3/1996 |
| WO | WO 99/53039 | 10/1999 |

OTHER PUBLICATIONS

Graham et al, Journal of Medicinal Chemistry, 1987, No. 30, pp. 1074–1090.
Stammers et al, Tetrahedron Letters, 1999, vol. 40, No. 17, pp. 3325–3328.
Scott et al, J. Organic Chemistry, 1981, vol. 46, No. 25, pp. 5086–5093.
Amino et al, Bull. Chemical Society of Japan, 1991, vol. 64, pp. 1040–1042.
Meek et al, J. American Chemical Society, 1955, 77, pp. 6675–6677.
Black et al, J. Chemistry Society (C), 1968, pp. 288–290.
Chenault et al, Journal of the American Chemical Society, 1989, vol. 111, pp. 6354–6364.
Hamon et al, Synthetic Communications, 1996, 26(6), pp. 1109–1115.
Myers et al, J. Am. Chem. Soc., 1997, vol. 119, pp. 656–673.
Burk et al, Transition Metals for Organic Synthesis, 1998, vol. 2, pp. 13–25.
Newham et al, Chem. Rev., 1963, 63, 123–137.
Greenstein et al, Chemistry of the Amino Acids, vol. 2, Wiley & Sons, New York, 1961, vol. 2, pp. 823–843.
Burk et al, J. Org. Chem. 1997, 62, pp. 7054–7057.
Schmidt et al, Synthesis, 1984, pp. 53–60.
Richards et al, Tetrahedron: Asymmetry, 1998, vol. 9, pp. 2377–2407.
Fiorini et al, Journal of Molecular Catalysis, 1979, vol. 5, pp. 303–310.
Pracejus et al, Tetrahedron Letters, 1977, vol. 39, pp. 3497–3500.
Marquarding et al, Journal of the American Chemical Society, 1970, vol. 92, pp. 5389–5393.
Armstrong et al, Analytical Chemistry, 1985, vol. 57, No. 2, pp. 481–484.
Boaz, Tetrahedron Letters, 1989, vol. 30, No. 16, pp. 2061–2064.
Hayashi et al, Bull Chemical Society of Japan, 1980, vol. 53, No. 4, pp. 1138–1151.
Schmidt et al, Synthesis, 1992, pp. 487–490.

* cited by examiner

Primary Examiner—Shailendra Kumar
Assistant Examiner—Paul A. Zucker
(74) Attorney, Agent, or Firm—Michael J. Blake; Bernard J. Graves, Jr.

(57) ABSTRACT

Disclosed are processes for the preparation of enantiomerically-enriched cyclopropylalanine derivatives by the hydrogenation of certain enamides in the presence of a catalyst comprising a transition metal and a substantially enantiomerically-pure bis-phosphine catalyst and certain novel enamide ester compounds which are intermediates in the processes. The processes include novel 2-step and 3-step processes for the preparation of enantiomerically-enriched cyclopropylalanine derivatives. The two-step process comprises the steps of reacting cyclopropanecarboxaldehyde with a substituted phosphorylglycine to afford an enamide ester which then is hydrogenated in the presence of a catalyst comprising a transition metal and a substantially enantiomerically-pure bis-phosphine catalyst. The three-step process comprises the steps of forming an azlactone from an N-acylglycine and cyclopropanecarboxaldehyde, converting the azlactone to the aforesaid enamide which then is hydrogenated in the presence of a catalyst comprising a transition metal and a substantially enantiomerically-pure bis-phosphine catalyst.

17 Claims, No Drawings

PROCESS FOR THE PREPARATION OF ENANTIOMERICALLY-ENRICHED CYCLOPROPYLALANINE DERIVATES

CROSS REFERENCE TO RELATED APPLICATION

This application claims the benefit of U.S. Provisional Application Ser. No. 60/236,544, filed Sep. 29, 2000.

FIELD OF THE INVENTION

This invention pertains to a process for the preparation of enantiomerically-enriched cyclopropylalanine derivatives. More specifically, this invention pertains to the synthesis of enantiomerically-enriched cyclopropylalanine derivatives by the hydrogenation of certain enamides in the presence of a catalyst comprising a transition metal and a substantially enantiomerically-pure bis-phosphine catalyst. The present invention also pertains to a novel 3-step process for the preparation of enantiomerically-enriched cyclopropylalanine derivatives comprising the steps of forming an azlactone from an N-acylglycine and cyclopropanecarboxaldehyde, converting the azlactone to the aforesaid enamide which then is hydrogenated in the presence of a catalyst comprising a transition metal and a substantially enantiomerically-pure bis-phosphine catalyst. In addition, the present invention pertains to a novel two-step process for the preparation of enantiomerically-enriched cyclopropylalanine derivatives comprising the steps of reacting cyclopropylcarboxaldehyde with a substituted phosphorylglycine to afford the aformentioned enamide which then is hydrogenated in the presence of a catalyst comprising a transition metal and a substantially enantiomerically-pure bis-phosphine catalyst. The present invention further pertains to certain novel intermediate enamide ester compounds which are intermediates in the process.

BACKGROUND OF THE INVENTION

Cyclopropylalanine and its derivatives are important intermediates in the synthesis of many valuable pharmaceuticals. For example, S. Thompson and coworkers (PCT Published Patent Application 99/53039) have identified a L-cyclopropylalanine-containing peptide as an effective cysteine protease inhibitor used for the treatment of parasitic diseases. Thus, an efficient and flexible synthesis of cyclopropylalanine derivatives in high yield and high enantiomeric purity is needed.

The synthesis of racemic cyclopropylalanine has been reported previously. Amino, Y., et al., *Bull. Chem. Soc. Jpn.* 1991, 64,1040–1042 describe the reaction of carbon monoxide and hydrogen with cyclopropane-methanol and acetamide in the presence of a cobalt catalyst to produce racemic N-acetyl cyclopropylalanine. Meek, J. S., et al., *J. Org. Chem.* 1955, 6675–6678; and Black, D., et al. *J. Chem. Soc.* (C), 1968, 288–289 disclose the hydrolysis of diethyl cyclopropylcarbinyl(formylamido)malonate to produce cyclopropylalanine after extensive work-up. However, no method for the preparation and/or isolation of enantiomerically enriched cyclopropylalanine is mentioned.

Chemoenzymatic syntheses of enantiomerically enriched cyclopropylalanine derivatives start from racemic cyclopropylalanine. For example, Chenault, H. K., et al. *J. Am. Chem. Soc.* 1989, 111, 6354–6464 disclose the isolation of L-cyclopropylalanine 1 after treatment of racemic N-acetyl-cyclopropylalanine with Acylase I. Alternatively, Harmon, C.; Rawlings, C. *Syn. Commun.* 1996, 26, 1109–1115 disclose the treatment of racemic N-acetyl-cyclopropylalanine with porcine pancreatic acylase I to produce L-cyclopropylalanine in the completely deprotected form. These enzymatic methods generally require several steps, e.g., greater than 6 synthetic steps, and the final step is limited to 50% yield.

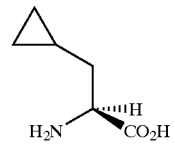

Myers, A. G.; Gleason, J. L.; Yoon, T.; Kung, D. W. *J. Am. Chem. Soc.* 1997, 119, 656–673, describe the asymmetric synthesis of both D- and L-cyclopropylalanine derivatives using an asymmetric alkylation of the lithium enolate of pseudoephedrine glycinamide 2 with cyclopropylmethyl bromide to provide the amino acid derivative 3. However, this method requires the use of a stoichiometric amount of an expensive chiral auxiliary and further synthetic manipulation is required to remove the auxiliary after alkylation. Additionally, two distinct starting materials must be used to isolate either R- or S-cyclopropylalanine. The (S,S)-pseudoephedrine derivative provides only the D-amino acid derivative, whereas the (R,R)-pseudoephedrine derivative must be used to isolate the amino acid in the L-configuration.

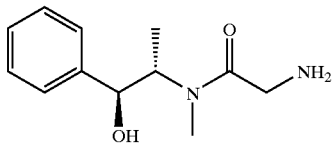

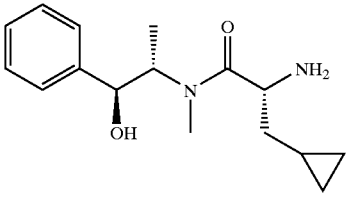

Transition-metal catalyzed asymmetric hydrogenation has been used extensively in the production of α-amino acids from the corresponding enamide esters. See, for example, Burk, M. J.; et al. in *Transition Metals for Organic Synthesis*, Beller, M., Bolm, C. Eds.; and Wiley-VCH: Basel, 1998; vol. 2, pg 13–25. Catalytic asymmetric hydrogenation of enamide esters has the advantage of the use of catalytic amounts (substrate to catalyst ratios of >100) of expensive chiral reagents as well as access to both R- and S-enantiomers of the α-amino acid from a common starting material. Additionally, in some cases, a variety of different functionalities are tolerated at both the amine and carboxyl termini of the amino acid precursor, which eliminates the need for further protecting group manipulations. However, catalytic asymmetric hydrogenation of cyclopropylalanine derivatives has not been reported in the literature. This deficiency is not surprising since hydrogenation of substrates containing cyclopropyl moieties is not trivial, as it is well known that transition metal-catalyzed hydrogenolysis of cyclopropyl groups occurs readily (Newham, *J. Chem. Rev.* 1963, 63,123–135).

BRIEF SUMMARY OF THE INVENTION

One embodiment of the present invention is a process for the preparation of an enantiomerically-enriched cyclopropylalanine compound having the formula

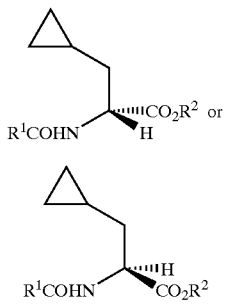

which comprises contacting an enamide having the formula

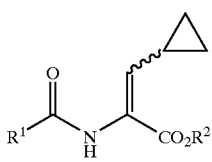

with hydrogen in the presence of a catalyst system comprising a transition metal and a substantially enantiomerically-pure bis-phosphine under hydrogenation conditions of pressure and temperature; wherein $R^1$ is hydrogen, substituted or unsubstituted $C_1$ to $C_{20}$ alkyl, substituted or unsubstituted $C_1$ to $C_{20}$ alkoxy, substituted or unsubstituted $C_3$ to $C_8$ cycloalkyl, substituted or unsubstituted $C_3$ to $C_8$ cycloalkoxy, substituted or unsubstituted carbocyclic $C_6$ to $C_{20}$ aryl, substituted or unsubstituted carbocyclic $C_6$ to $C_{20}$ aryloxy, substituted or unsubstituted $C_4$ to $C_{20}$ heteroaryl wherein the heteroatoms are selected from sulfur, nitrogen, and oxygen or substituted or unsubstituted $C_4$ to $C_{20}$ heteroaryloxy wherein the heteroatoms are selected from sulfur, nitrogen, and oxygen; and $R^2$ is hydrogen, substituted or unsubstituted $C_1$ to $C_{20}$ alkyl, substituted or unsubstituted $C_3$ to $C_8$ cycloalkyl, substituted or unsubstituted carbocyclic $C_6$ to $C_{20}$ aryl, or substituted or unsubstituted $C_4$ to $C_{20}$ heteroaryl wherein the heteroatoms are selected from sulfur, nitrogen, and oxygen. This embodiment of our invention is unique since it produces an enantiomerically-enriched cyclopropylalanine compound without significant hydrogenolysis of the cyclopropyl ring.

Another embodiment of the present invention is a process for the preparation of an enantiomerically-enriched cyclopropylalanine compound having formula 4 or 5 by means of a novel combination of steps comprising (1) contacting cyclopropanecarboxaldehyde (CPCA) with an N-acylglycine having the formula

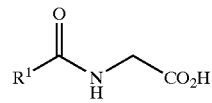

in the presence of a carboxylic acid anhydride and a base at elevated temperature to produce an azlactone having the formula

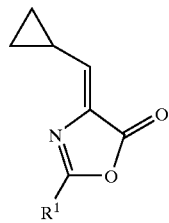

(2) contacting azlactone 8 with an alcohol optionally in the presence of an alkali or alkaline earth metal alkoxide or hydroxide to produce an enamide having the formula

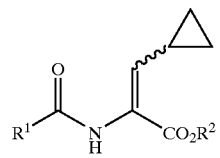

and (3) contacting enamide 6 with hydrogen in the presence of a catalyst system comprising a transition metal and a substantially enantiomerically-pure bis-phosphine under hydrogenation conditions of pressure and temperature; wherein $R^1$ and $R^2$ are defined above.

A third embodiment of the present invention involves a process for the preparation of an enantiomerically-enriched cyclopropylalanine compound having formula 4 or 5 by means of another novel combination of steps comprising
(i) contacting cyclopropanecarboxaldehyde (CPCA) with an N-acylglycine having the formula

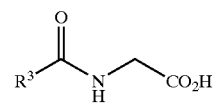

in the presence of a carboxylic acid anhydride at elevated temperature to produce an azlactone having the formula

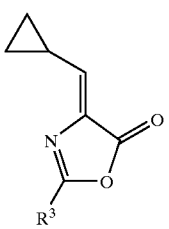

(ii) contacting azlactone 10 with an alcohol optionally in the presence of an alkali or alkaline earth metal alkoxide or hydroxide to produce an enamide having the formula

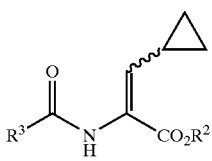

11

(iii) contacting enamide 11 with an acylating agent having the formula $R^4O—C(O)—O—C(O)—OR^4$ or $R^4O—C(O)—X$ wherein X is fluorine, chlorine, bromine, or iodine in the presence of 4-(N,N-dimethylamino)pyridine (DMAP) and an inert (non-reactive) organic solvent to produce an amido-carbamate having formula 12

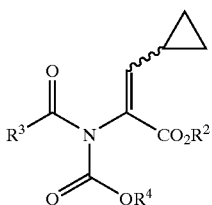

12

(iv) contacting amido-carbamate 12 with a nucleophile in the presence of an inert (non-reactive) organic solvent to produce a second enamide having formula 13

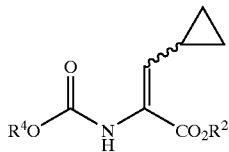

13 and (iv) contacting enamide 13 with hydrogen in the presence of a catalyst system comprising a transition metal and a substantially enantiomerically-pure bis-phosphine under hydrogenation conditions of pressure and temperature;

wherein $R^2$ is defined above; and $R^3$ and $R^4$ are independently selected from substituted and unsubstituted $C_1$ to $C_{20}$ alkyl, substituted and unsubstituted $C_3$ to $C_8$ cycloalkyl, substituted and unsubstituted carbocyclic $C_6$ to $C_{20}$ aryl, substituted and unsubstituted $C_4$ to $C_{20}$ heteroaryl wherein the heteroatoms are selected from sulfur, nitrogen, and oxygen.

A fourth embodiment of the invention concerns a process for the preparation of an enantiomerically-enriched cyclopropylalanine compound having formula 4 or 5 by means of a novel combination of steps comprising (a) reacting cyclopropanecarboxaldehyde with a phosphonate ester having formula 19:

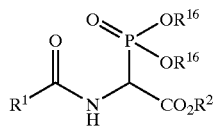

19 in the presence of a base in an inert organic solvent to produce enamide 6

6 and (b) contacting enamide 6 with hydrogen in the presence of a catalyst system comprising a transition metal and a substantially enantiomerically-pure bis-phosphine under hydrogenation conditions of pressure and temperature; wherein $R^1$ and $R^2$ are as defined above; and $R^{16}$ is selected from substituted and unsubstituted $C_1$ to $C_{20}$ alkyl, substituted and unsubstituted $C_3$ to $C_8$ cycloalkyl, substituted and unsubstituted carbocyclic $C_6$ to $C_{20}$ aryl, substituted and unsubstituted $C_4$ to $C_{20}$ heteroaryl wherein the heteroatoms are selected from sulfur, nitrogen, and oxygen.

Additional embodiments of our invention are represented by the enamides of formulas 6 and 13 which are novel compositions of matter.

DETAILED DESCRIPTION OF THE INVENTION

The first embodiment of the present invention provides for the preparation of an enantiomerically-enriched cyclopropylalanine compound having formula 4 or 5 by contacting an enamide having formula 6 with hydrogen in the presence of a catalyst system comprising a transition metal and a substantially enantiomerically-pure bis-phosphine under hydrogenation conditions of pressure and temperature. This embodiment of our invention is unique since it produces an enantiomerically-enriched cyclopropylalanine compound without significant hydrogenolysis of the cyclopropyl ring. Examples of the transition metal component of the catalyst include ruthenium, rhodium and iridium with ruthenium and rhodium being preferred. Examples of the bis-phosphine component of the catalyst include, but are not limited to, either substantially pure enantiomer or diastereomer of 2,3-O-isopropylidene-2,3-dihydroxy-1,4-bis(diphenylphosphino)butane (DIOP), 2,2'-bis(diphenylphosphino)-1,1'-binaphthyl (BINAP), 1,2-bis-(2,5-dialkylphospholano)benzene (DuPHOS), 1,2-bis-2,5-dialkylphospholano(ethane) (BPE), 2,3-bis-(diphenylphosphino)butane (CHIRAPHOS), 2-diphenylphosphinomethyl-4-diphenylphosphino-1-t-butoxycarbonylpyrrolidine (BPPM) and certain bis-phosphine compounds comprising a substantially enantiomerically pure chiral backbone linking two phosphine residues wherein one of the phosphine residues has three phosphorus-carbon bonds and the other phosphine residue has two phophorus-carbon bonds and one phosphorus-nitrogen bond wherein the nitrogen is part of the chiral backbone, e.g., N-alkyl-N-diphenylphosphino-1-[2-

(diphenylphosphino)ferrocenyl]ethylamine. The bis-phosphine component preferably is N-alkyl-N-diphenylphosphino-1-[2-(diphenylphosphino)ferrocenyl]alkylamine wherein each alkyl group independently contains 1 to 6 carbon atoms, e.g., N-methyl-N-diphenylphosphino-1-[2-(diphenylphosphino)ferrocenyl]ethylamine, and 1,2-bis-(2,5-dialkylphospholano)benzene (DuPHOS) wherein each alkyl group contains 1 to 6 carbon atoms. The ratio of gram-atoms of transition metal to gram-moles of bis-phosphine may be in the range of about 0.1:1 to 2:1,preferably about 0.8:1. The active catalyst comprises a complex of the transition metal and the bis-phosphine and may be formed in situ prior to asymmetric hydrogenation or formed and isolated independently.

Except for the novel phosphinoamino-phosphines described below, the substantially enantiomerically-pure bis-phosphines described above are known compositions of matter and can be obtained commercially and/or prepared according to known procedures. The novel phosphinoamino-phosphines which may be employed in the present invention are substantially enantiomerically pure bis-phosphine compounds comprising a substantially enantiomerically pure chiral backbone linking two phosphine residues wherein one of the phosphine residues has three phosphorus-carbon bonds and the other phosphine residue has two phophorus-carbon bonds and one phosphorus-nitrogen bond wherein the nitrogen is part of the chiral backbone. These compounds are the first examples of chiral bis-phosphines combining a tri-hydrocarbylphosphine with a dihydrocarbyl-aminophosphine. Examples of the substantially enantiomerically pure, i.e., an enantiomeric excess of 90% or greater, phosphinoamino-phosphine compounds include phosphinometallocenyl-aminophosphines having the general formulas 14 and 15 (the enantiomer of 14):

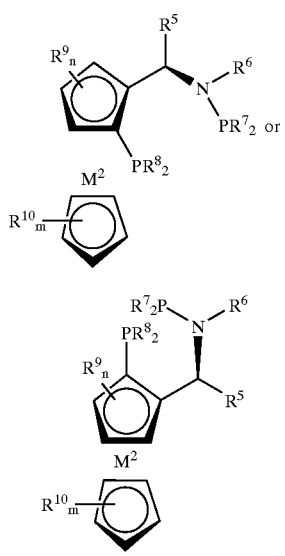

14

15 wherein
R$^5$ is selected from substituted and unsubstituted, branched- and straight-chain C$_1$ to C$_{20}$ alkyl, substituted and unsubstituted C$_3$ to C$_8$ cycloalkyl, substituted and unsubstituted C$_6$ to C$_{20}$ carbocyclic aryl, and substituted and unsubstituted C$_4$ to C$_{20}$ heteroaryl wherein the heteroatoms are selected from sulfur, nitrogen, and oxygen;
R$^6$, R$^7$, R$^8$, R$^9$, and R$^{10}$ are independently selected from hydrogen, substituted and unsubstituted, branched- and straight-chain C$_1$ to C$_{20}$ alkyl, substituted and unsubstituted C$_3$ to C$_8$ cycloalkyl, substituted and unsubstituted C$_6$ to C$_{20}$ carbocyclic aryl, and substituted and unsubstituted C$_4$ to C$_{20}$ heteroaryl wherein the heteroatoms are selected from sulfur, nitrogen, and oxygen;

n is 0 to 3;

m is 0 to 5; and

M$^2$ is selected from the metals of Groups IVB, VB, VIB, VIIB and VIII. Examples of the groups which R$^5$, R$^6$, R$^7$, R$^8$, R$^9$, and R$^{10}$ may represent are given below in the description of the R$^1$ and R$^2$ radicals. The substantially enantiomerically pure, phosphinometallocenyl-aminophosphines which presently are preferred have formulas 14 and 15 wherein R$^5$ is C$_1$ to C$_6$ alkyl; R$^6$ is hydrogen or C$_1$ to C$_6$ alkyl; R$^7$ and R$^8$ are aryl, most preferably phenyl; R$^9$ and R$^{10}$ are hydrogen; and M$^2$ is iron, ruthenium, or osmium, most preferably iron.

The bis-phosphine 14 may be prepared by the steps comprising:
(1) contacting a dialkyl amine having formula 16:

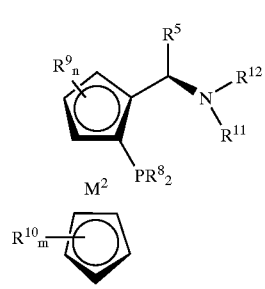

16 with a carboxylic anhydride having the formula (R$^{13}$CO)$_2$O to obtain an ester compound having formula 17:

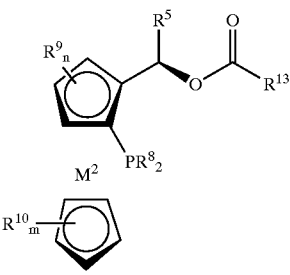

17

(2) contacting the ester produced in step (1) with an amine having the formula H$_2$N—R$^6$ to obtain an intermediate amino-phosphine compound having formula 18:

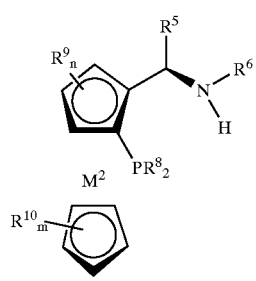

18

(3) contacting intermediate compound 18 with a halophosphine having the formula X—P(R⁷)₂;

wherein $R^5$, $R^6$, $R^7$, $R^8$, $R^9$, $R^{10}$, n, m, and $M^2$ are defined hereinabove, $R^{11}$ and $R^{12}$ are independently selected from substituted and unsubstituted, branched- and straight-chain $C_1$ to $C_{20}$ alkyl, substituted and unsubstituted $C_3$ to $C_8$ cycloalkyl, substituted and unsubstituted $C_6$ to $C_{20}$ carbocyclic aryl, and substituted and unsubstituted $C_4$ to $C_{20}$ heteroaryl wherein the heteroatoms are selected from sulfur, nitrogen, and oxygen, $R^{13}$ is a $C_1$ to $C_4$ alkyl radical, and X is chlorine, bromine, or iodine. The compounds of formula 15 may be prepared when dialkylamine having formula 19:

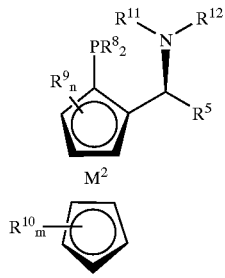

is used as the starting material affording intermediates 20 and 21 analogous to 17 and 18, respectively.

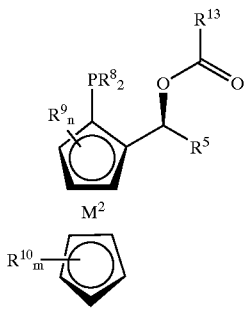

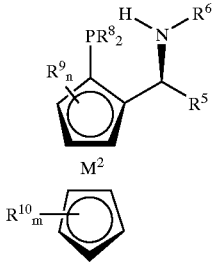

The hydrogenation reaction is carried out in the presence of one or more inert (non-reactive) organic solvent. Examples of inert solvents include aliphatic hydrocarbons such as hexane, heptane, octane and the like, aromatic hydrocarbons such as toluene, xylenes and the like, cyclic and acyclic ethers such as tert-butyl methyl ether, diisopropyl ether, tetrahydrofuran and the like, lower alcohols such as methanol, ethanol, n-propanol, isopropanol, n-butanol and the like, halogenated aliphatic or aromatic hydrocarbons such as dichloromethane, tetrachloroethylene, chloroform, chlorobenzene and the like, dialkyl ketones such as acetone, 2-butanone, 3-pentanone, methyl isopropyl ketone, methyl isobutyl ketone and the like, and polar aprotic solvents such as dimethylformamide, dimethyl sulfoxide and the like. Tetrahydrofuran and acetone are preferred solvents. The hydrogenation may be carried out using enamide 6 (or 13) concentrations between about 0.01 M to 10 M, preferably about 0.1 to 3 M.

The hydrogenation conditions of pressure and temperature which may be used in the hydrogenation of enamides 6 or 13 may be in the range of about 0.5 to 69 bars gauge (barg, approximately 7 to 1000 pounds per square inch gauge—psig) hydrogen pressure and about −20 to 100° C. The hydrogenation conditions preferably are a hydrogen pressure of about 0.69 to 20.7 barg (approximately 10 to 300 psig) and a temperature of 10 to 35° C. The reaction may be run until the majority of the olefin of the enamide is hydrogenated to the α-amino acid derivative.

The alkyl groups which may be represented by each of $R^1$ and $R^2$ may be straight- or branched-chain, aliphatic hydrocarbon radicals containing up to about 20 carbon atoms and may be substituted, for example, with one to three groups selected from $C_1$ to $C_6$ alkoxy, $C_1$ to $C_6$ alkylthio, cyano, nitro, $C_2$ to $C_6$ alkoxycarbonyl, $C_2$ to $C_6$ alkanoyloxy, aryl and halogen. The terms "$C_1$ to $C_6$ alkoxy", "$C_1$ to $C_6$ alkylthio", "$C_2$ to $C_6$ alkoxycarbonyl", and "$C_2$ to $C_6$ alkanoyloxy" are used to denote radicals corresponding to the structures —$OR^{14}$, —$SR^{14}$, —$CO_2R^{14}$, and —$OCOR^{14}$, respectively, wherein $R^{14}$ is $C_1$ to $C_6$ alkyl or substituted $C_1$ to $C_6$ alkyl. The term "$C_3$ to $C_8$ cycloalkyl" is used to denote a saturated, carbocyclic hydrocarbon radical having three to eight carbon atoms. The aryl groups which each of $R^1$ and $R^2$ may represent may include phenyl and phenyl substituted with one to three substituents selected from $C_1$ to $C_6$ alkyl, substituted $C_1$ to $C_6$ alkyl, $C_1$ to $C_6$ alkoxy, halogen, carboxy, cyano, $C_1$ to $C_6$ alkanoyloxy, $C_1$ to $C_6$ alkylthio, $C_1$ to $C_6$ alkylsulfonyl, trifluoromethyl, hydroxy, $C_2$ to $C_6$ alkoxycarbonyl, $C_2$ to $C_6$ alkanoylamino and —O—$R^{15}$, S—$R^{15}$, —$SO_2$—$R^{15}$, —$NHSO_2R^{15}$ and —$NHCO_2R^{15}$, wherein $R^{15}$ is phenyl or phenyl substituted with one to three groups selected from $C_1$ to $C_6$ alkyl, $C_1$ to $C_6$ alkoxy and halogen.

The heteroaryl radicals include a 5- or 6-membered aromatic ring containing one to three hetero atom selected from oxygen, sulfur and nitrogen. Examples of such heteroaryl groups are thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benothiazolyl, benzimidazolyl, indolyl and the like. The heteroaryl radicals may be substituted, for example, with up to three groups such as $C_1$ to $C_6$ alkyl, $C_1$ to $C_6$ alkoxy, substituted $C_1$ to $C_6$ alkyl, halogen, $C_1$ to $C_6$ alkylthio, aryl, arylthio, aryloxy, $C_2$ to $C_6$ alkoxycarbonyl and $C_2$ to $C_6$ alkanoylamino. The heteroaryl radicals also may be substituted with a fused ring system, e.g., a benzo or naphtho residue, which may be unsubstituted or substituted, for example, with up to three of the groups set forth in the preceding sentence. The term "halogen" is used to include fluorine, chlorine, bromine, and iodine.

The alkoxy groups which $R^1$ may represent may be straight- or branched-chain, aliphatic hydrocarbon radicals containing up to about 20 carbon atoms and may be substituted, for example, with one to three groups selected from $C_1$ to $C_6$ alkoxy, $C_1$ to $C_6$ alkylthio, cyano, nitro, $C_2$ to $C_6$ alkoxycarbonyl, $C_2$ to $C_6$ alkanoyloxy, aryl and halogen. The term "$C_3$ to $C_8$ cycloalkoxy" is used to denote a saturated, carbocyclic hydrocarbyloxy radical having three to eight carbon atoms. The aryloxy groups which $R^1$ may represent may include phenoxy and phenoxy substituted with one to three substituents selected from $C_1$ to $C_6$ alkyl, substituted $C_1$ to $C_6$ alkyl, $C_1$ to $C_6$ alkoxy, halogen, carboxy, cyano, $C_1$ to $C_6$ alkanoyloxy, $C_1$ to $C_6$ alkylthio, $C_1$ to $C_6$ alkylsulfonyl, trifluoromethyl, hydroxy, $C_2$ to $C_6$ alkoxycarbonyl, $C_2$ to $C_6$ alkanoylamino and —O—$R^{15}$, S—$R^{15}$, —$SO_2$—$R^{15}$, —$NHSO_2R^{15}$ and —$NHCO_2R^{15}$, wherein $R^{15}$ is defined above.

The heteroaryloxy radicals include a 5- or 6- membered aromatic ring containing one to three hetero atom selected from oxygen, sulfur and nitrogen wherein a ring carbon atom is bonded to the linking oxygen atom of the heteroaryloxy radical. Examples of such heteroaryl groups are thienyloxy, furyloxy, pyrrolyloxy, imidazolyloxy, pyrazolyloxy, thiazolyloxy, isothiazolyloxy, oxazolyloxy, isoxazolyloxy, triazolyloxy, thiadiazolyloxy, oxadiazolyloxy, tetrazolyloxy, pyridyloxy, pyrimidyloxy, benzoxazolyloxy, benothiazolyloxy, benzimidazolyloxy, indolyloxy and the like. The heteroaryloxy radicals may be substituted, for example, with up to three groups such as $C_1$ to $C_6$ alkyl, $C_1$ to $C_6$ alkoxy, substituted $C_1$ to $C_6$ alkyl, halogen, $C_1$ to $C_6$ alkylthio, aryl, arylthio, aryloxy, $C_2$ to $C_6$ alkoxycarbonyl and $C_2$ to $C_6$ alkanoylamino. The heteroaryloxy radicals also may be substituted with a fused ring system, e.g., a benzo or naphtho residue, which may be unsubstituted or substituted in the manner described above for the heteroaryl substitutents. $R^1$ preferably represents $C_1$ to $C_6$ alkyl, phenyl, tolyl, $C_1$ to $C_6$ alkoxy, or benzyloxy; and $R^2$ preferably represents $C_1$ to $C_6$ alkyl or benzyl.

A second embodiment of the invention concerns a process for the preparation of an enantiomerically-enriched cyclopropylalanine compound having formula 4 or 5 by means of a novel combination of steps comprising (1) contacting cyclopropanecarboxaldehyde (CPCA) with an N-acylglycine having the formula

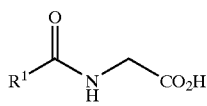

7 in the presence of a carboxylic acid anhydride and a base at elevated temperature to produce an azlactone having the formula

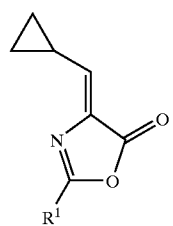

8

(2) contacting azlactone 8 with an alcohol optionally in the presence of an alkali or alkaline earth metal alkoxide or hydroxide to produce an enamide having the formula

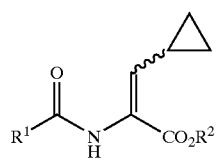

6 and (3) contacting enamide 6 with hydrogen in the presence of a catalyst system comprising a transition metal and a substantially enantiomerically-pure bis-phosphine under hydrogenation conditions of pressure and temperature; wherein $R^1$ and $R^2$ are defined above.

In step (1) CPCA is reacted or condensed with N-acylglycine 7 to form azlactone 8 using variations of the Erylenmeyer synthesis (Greenstein, J. P.; Winitz, M. in *Chemistry of the Amino Acids*, Vol. 2, Wiley & Sons: New York, 1961;vol. 2,pg 823–843). N-acylglycines of formula 7 may be purchased and/or may be prepared according to published procedures, e.g., by acylating glycine with known acylating agents such as carboxylic acid anhydrides and acid halides and chloroformate esters. The mole ratio of CPCA:N-acylglycine 7 may be in the range of about 1:1 to 10:1 and preferably is in the range of about 2:1 to 3:1. Step (1) is carried out in the presence of an alkanoic (aliphatic carboxylic) acid anhydride containing 4 to 8 carbon atoms, most preferably acetic anhydride. The amount of alkanoic anhydride used may be about 2 to 10 moles equivalents, preferably about 3 moles, per mole of N-acylglycine 7. Step (1) preferably is carried out in the presence of a base such as alkanoates, carbonates and bicarbonates of the alkali metals and alkaline earth metals. Specific examples of such bases include the acetates, carbonates and bicarbonates of lithium, sodium, potassium, cesium, magnesium, calcium, lead and barium. The base preferably is sodium acetate. The amount of base may be between 0.1 and 5 equivalents, preferably 1.5-equivalents, of base per equivalent of N-acylglycine 7. Step (1) normally is carried out at a temperature of about 35 to 150° C., preferably about 85 to 110° C. Pressure is not an important factor in the condensation of step (1) and, thus, step (1) normally is carried out at ambient pressure although pressures moderately above or below ambient may be employed if desired. The reaction may be run until substantially all of N-acylglycine 7 is converted to azlactone 8. Azlactone 8 is isolated using standard technologies known to those in the art, e.g. extraction, concentration, precipitation.

Step (2) of the process comprises contacting azlactone 8 with an alcohol optionally in the presence of an alkali or alkaline earth metal alkoxide or hydroxide to produce an enamide having the formula

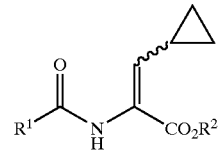

6

The alkali or alkaline earth metal may be lithium, potassium, sodium, cesium and the like but preferably is sodium or potassium. The amount of alkoxide or hydroxide employed may be in the range of about 0 to 10 moles alkoxide or hydroxide per mole of azlactone 8. The reaction can be run with or without an inert (non-reactive) organic solvent. Examples of the optional solvents include aliphatic hydrocarbons such as hexane, heptane, octane and the like, and aromatic hydrocarbons such as benzene, toluene, xylene and the like. The concentration of azlactone 8 may be between 0.01 to 10M. In a preferred embodiment, step (2) is carried out in benzyl alcohol with 0.05 equivalents of sodium methoxide. If the carboxylic acid is desired ($R^2$=H), any metal hydroxide, carbonate or bicarbonate base such as lithium, sodium, potassium, cesium, magnesium, calcium, and barium may be used, preferably in aqueous solution. The resulting carboxylate salt can be neutralized to afford the desired carboxylic acid.

Step (2) may be carried out at a temperature in the range of about −10 and 100° C. with preferred embodiment at 25–50° C. Again, pressure is not an important factor in the reaction of step (2) and, thus, step (2) normally is carried out at ambient pressure although pressures moderately above or below ambient may be employed if desired. The reaction may be run until the majority of the azlactone is converted to enamide ester.

Step (3) of the 3-step embodiment of our invention is carried out according to the procedure described above for the first embodiment.

The third embodiment of the invention is a modification of the second embodiment and provides a process for the preparation of an enantiomerically-enriched cyclopropylalanine compound having formula 4 or 5 by means of another novel combination of steps comprising (i) contacting cyclopropanecarboxaldehyde (CPCA) with an N-acylglycine having the formula

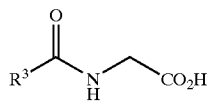

9 in the presence of a carboxylic acid anhydride and a base at elevated temperature to produce an azlactone having the formula

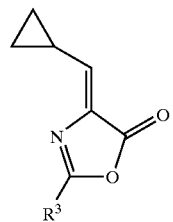

10

(ii) contacting azlactone 10 with an alcohol optionally in the presence of an alkali or alkaline earth metal alkoxide or hydroxide to produce an enamide having the formula

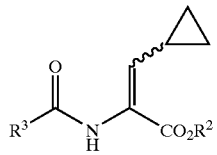

11

(iii) contacting enamide 11 with an acylating agent having the formula $R^4O—C(O)—O—C(O)—OR^4$ or $R^4O—C(O)—X$ where X is fluorine, chlorine, bromine, or iodine in the presence of 4-(N,N-dimethylamino)pyridine (DMAP) and an inert (non-reactive) organic solvent to produce an amido-carbamate having the formula 12

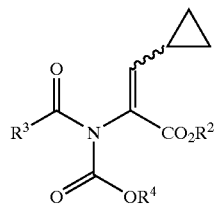

12

(iv) contacting amido-carbamate 12 with a nucleophile in the presence of an inert (non-reactive) organic solvent to produce a second enamide having formula 13

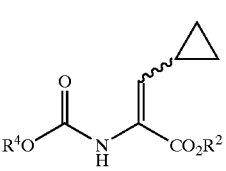

13 and (v) contacting enamide 13 with hydrogen in the presence of a catalyst system comprising a transition metal and a substantially enantiomerically-pure bis-phosphine under hydrogenation conditions of pressure and temperature; wherein $R^2$ is defined above; and $R^3$ and $R^4$ are independently selected from substituted and unsubstituted $C_1$ to $C_{20}$ alkyl, substituted and unsubstituted $C_3$ to $C_8$ cycloalkyl, substituted and unsubstituted carbocyclic $C_6$ to $C_{20}$ aryl, substituted and unsubstituted $C_4$ to $C_{20}$ heteroaryl wherein the heteroatoms are selected from sulfur, nitrogen, and oxygen.

This embodiment is particularly useful for preparing α-amino acid derivatives wherein the nitrogen substituent is a carbamate. These species are particularly advantaged for standard solution and solid-phase peptide synthesis.

Steps (i), (ii) and (v) of the third embodiment process are carried out in a manner substantially identical to steps (1), (2) and (3) of the second embodiment of the invention. The primary difference is that in the third embodiment the acyl residue of the N-acylglycine reactant is a group having the formula —CO—$R^3$ wherein $R^3$ is an alkyl, cycloalkyl, carbocyclic aryl or heterocyclic aryl radical but not an alkoxy, etc. radical. In step (iii) enamide 11 is contacted with an acylating agent having the formula $R^4O—C(O)—O—C(O)—OR^4$, e.g., di-tert-butyl dicarbonate, or $R^4O—C(O)—X$ where X is fluorine, chlorine, bromine, or iodine in the presence of 4-(N,N-dimethylamino)pyridine (DMAP) and an inert (non-reactive) organic solvent to produce an amido-carbamate 12. Step (iii) can be carried out at a temperature of about −20 to 45° C., preferably 15 to 35° C. according to the general procedure described by Burk, M. J.; Allen, J. G. *J. Org. Chem.* 1997, 62, 7054–7057. The amount of dicarbonate or haloformate acylating agent used can be about 1.8 to 10 equivalents, preferably about 2 to 4 equivalents of dicarbonate acylating agent per mole of enamide 11. The amount of DMAP used typically is between about 0.1 and 1 equivalents, preferably 0.2 to 0.4 equivalents of DMAP per mole of enamide 11. The inert, organic solvent may be any non-reactive solvent including aliphatic hydrocarbons such as hexane, heptane, octane and the like; cyclic and acyclic ethers such as tert-butyl methyl ether, diisopropyl ether, tetrahydrofuran and the like; aromatic hydrocarbons such as benzene, toluene, xylene and the like; and polar aprotic solvents such as dimethylformamide, N-methylpyrrolidone, acetonitrile and the like. The solvent preferably is a cyclic or acylic ether with tetrahydrofuran being especially preferred. Once the reaction is determined to be sufficiently complete, excess acylating agent is quenched with a $C_1$ to $C_3$ alkanol such as methanol, ethanol and the like, preferably methanol. The amount of alkanol added may be from about 1 to 100 equivalents based on the amount of acylating agent used, with the preferred embodiment being two equivalents of alkanol.

Step (iv) comprises contacting amido-carbamate 12 with a nucleophile to produce a second enamide 13. Step (iv) may be carried out without isolating 12 from the crude reaction mixture resulting from step (iii). The reaction is generally carried out in an alkanol solvent such as methanol, ethanol, and the like, with methanol especially preferred. Normally, the reaction mixture should be cooled before the addition of the nucleophile. Step (iv) typically is carried out at a temperature in the range of about −40 and 15° C., preferably between −5 and 50° C. The nucleophile may be any alkali metal or alkaline earth metal hydroxide such as lithium, sodium, potassium, cesium, magnesium, calcium, and barium hydroxide or an amine such as pyridine, morpholine, hydrazine or hydrazine hydrate. Anhydrous hydrazine or hydrazine hydrate are the preferred nucleophiles. The amount of nucleophile may be between 1 and 50 equivalents with the preferred embodiment of 3–5 equivalents based on the amount of amido-carbamate 12.

Step (v) of the third embodiment of the invention is carried out by hydrogenating the second enamide 13 according to the hydrogenation procedures described herein.

A fourth embodiment of the invention concerns a process for the preparation of an enantiomerically-enriched cyclopropylalanine compound having formula 4 or 5 by means of a novel combination of steps comprising (a) reacting cyclopropanecarboxaldehyde with a phosphonate ester having the formula 19:

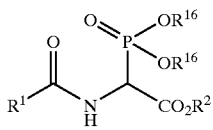

19 in the presence of a base and an inert organic solvent to produce enamide 6

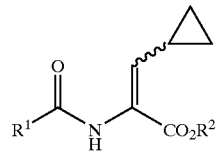

6 and (b) contacting enamide 6 with hydrogen in the presence of a catalyst system comprising a transition metal and a substantially enantiomerically-pure bis-phosphine under hydrogenation conditions of pressure and temperature; wherein $R^1$ and $R^2$ are as defined above; and $R^{16}$ is selected from substituted and unsubstituted $C_1$ to $C_{20}$ alkyl, substituted and unsubstituted $C_3$ to $C_8$ cycloalkyl, substituted and unsubstituted carbocyclic $C_6$ to $C_{20}$ aryl, and substituted and unsubstituted $C_4$ to $C_{20}$ heteroaryl wherein the heteroatoms are selected from sulfur, nitrogen, and oxygen.

In step (a), CPCA is reacted or condensed with phosphonate ester 19 in a Horner-Emmons Wittig reaction. The phosphonate ester 19 can be prepared by methods known in the art as in Schmidt, U.; Lieberknecht, A.; Wild, J., *Synthesis* 1984, 53–60. This type of Horner-Emmons reaction has also been reported by Schmidt, U.;Griesser, H.; Leitenberger, V.; Lieberknecht, A.; Mangold, R.; Meyer, R.; Riedl, B. *Synthesis* 1992, 487–490,although CPCA has not been used previously in this reaction. The amount of phosphonate ester generally is about 0.5 to 3 molar equivalents based on the amount of CPCA, and preferably is about 0.6–1.2 molar equivalents. The base employed in step (a) may be chosen from alkoxides of the alkali metals and alkaline earth metals and amines. Specific examples of alkoxide bases include the methoxide, ethoxide, isopropoxide, and t-butoxide of lithium, sodium, potassium, cesium, magnesium, calcium, lead and barium. Amine bases include 1,4-diazabicyclo[4.3.0]non-5-ene (DBN), 1,8-diazabicyclo[5.4.0]undec-7-ene (DBU), 1,4-diazabicyclo[2.2.2]-octane (DABCO), and tetramethylguanidine (TMG). The base preferably is tetramethylguanidine. The reaction typically is carried out in the presence of an inert organic solvent. This solvent may be any non-reactive solvent including aliphatic hydrocarbons such as hexane, heptane, octane and the like; cyclic and acyclic ethers such as tert-butyl methyl ether, diisopropyl ether, tetrahydrofuran and the like; aromatic hydrocarbons such as benzene, toluene, xylene and the like; esters such as methyl acetate, ethyl acetate, isopropyl acetate and the like; and polar aprotic solvents such as dimethylformamide, N-methylpyrrolidone, acetonitrile and the like. Tetrahydrofuran and ethyl acetate are preferred solvents. The reaction may be carried out at a temperature between −78° C. and the boiling point of the solvent, preferably between −20° C. and 30° C.

Step (b) of the fourth embodiment of the invention is carried out by hydrogenating enamide 6 according to the hydrogenation procedures described herein.

As noted hereinabove, enamides 6 and 13 are believed to be novel compositions.

EXAMPLES

The operation of the novel processes and preparation of the novel compounds provided by the present invention are further illustrated by the following examples.

Example 1

A 2.0 L, three-necked, round-bottom flask fitted with a condenser, mechanical stirrer and glass stopper was charged with N-benzoylglycine (hippuric acid, 100 g, 0.558 mol), sodium acetate (1.5 eq, 69 g), and acetic anhydride (6 eq, 318 mL) under an inert atmosphere. CPCA (3 eq, 126 mL) was added to the mixture at 25° C. Once the addition was complete, the reaction mixture was heated to 110° C. After 1.5 hours, the reaction was cooled to 50° C. Volatile materials were removed by vacuum distillation. The residue was dissolved in toluene (650 mL) and washed with water (500 mL×3). The toluene solution was concentrated by distillation (white precipitate formed as toluene was removed). The remaining thick slurry was filtered (isolated 16.5 g) and the filtrate further concentrated and filtered to isolate 18.5 g. The product thus produced was azlactone 8 wherein $R^1$ is phenyl. It was isolated as an off-white solid (35 g, 30%). $^1$H NMR (CDCl$_3$, 300 MHz) δ8.09–8.07 (m, 2H); 7.60–7.46 (m, 3H); 6.17–6.13 (d, J=10.8 Hz, 1H); 2.46–2.35 (m, 1H); 1.29–1.23 (m, 2H); 0.96–0.91 (m, 2H). $^{13}$C NMR (CDCl$_3$,75 MHz)

δ165.9; 161.7; 145.4; 134.3; 132.7; 128.8; 127.8; 125.8; 110.7; 13.5; 11.1.

Example 2

A 500 mL flask was charged with the azlactone (9.00 g, 42 mmol) from Example 1 and sodium methoxide in methanol (0.12 M, 1.1 eq, 385 mL) was added at 25° C. After 15 hours, the reaction was quenched with acetic acid (5 mL) and concentrated at reduced pressure. The crude product was recrystallized from ethyl acetate (50 mL) to provide enamide 6 wherein $R^1$ is phenyl and $R^2$ is methyl as a white powder (8.9 g, 87%). $^1$H NMR (CDCl$_3$,300 MHz) δ7.91–7.89 (d, J=6.9 Hz, 2H), 7.55–7.45 (m, 3H), 6.25–6.22 (d, J=11.1 Hz, 1H), 3.78 (s, 3H), 1.71–1.64 (m, 1H), 1.08–1.03 (m, 2H), 0.77–0.73 (m, 2H); $^{13}$C NMR (CDCl$_3$,75 MHz) δ144.1, 131.9, 128.7, 127.4,110.8, 52.3, 12.6, 8.9.

Example 3

A 50 mL flask was charged with the azlactone (1.00 g, 4.7 mmol) from Example 1,toluene (0.3 M, 15.6 mL) and benzyl alcohol (1.1 eq, 0.534 mL). Sodium methoxide (0.05 eq, 13 mg) was added to the slurry at 25° C. After 30 minutes, the wet solid was filtered and washed with toluene(5 mL). The product, enamide 6 wherein $R^1$ is phenyl and $R^2$ is benzyl, was isolated as a white amorphous solid (1.66 g) still wet with toluene and was used without further purification. $^1$H NMR (CDCl$_3$,300 MHz) δ7.90–7.85 (m, 2H), 7.61–7.25 (m, 3H), 6.27–6.24 (d, J=11.1 Hz, 1H), 5.19 (s, 2H), 1.83–1.57 (m, 1H), 1.05–1.02 (m, 2H), 0.72–0.70 (m, 2H); $^{13}$C NMR (CDCl$_3$,75 MHz) δ177.0; 164.5; 144.5; 128.6; 128.4; 128.2; 127.3; 67.1; 65.3; 44.4; 12.6; 8.9

Example 4

A 500 mL flask was charged with the enamide (5.0 g, 20.3 mmol) from Example 2, DMAP (0.2 eq, 500 mg) and anhydrous tetrahydrofuran (THF, 70 mL) under an inert atmosphere. Di-tert-butyl dicarbonate (2 eq, 8.9 g) was added to the solution at 25° C. and the reaction mixture was stirred at 25° C. overnight (17 hours). The solution was diluted with ethyl acetate (300 mL) and washed with water (2×300 mL), 0.05M HCl (1×300 mL), dried with magnesium sulfate and concentrated to provide a viscous yellow syrup (8.3 g). A portion of the product (1.0 g, 2.9 mmol) was diluted with methanol (10 mL) and cooled to 0° C. in an ice bath. 55% Aqueous hydrazine hydrate (4 eq, 0.66 mL) was added slowly over 2 minutes. The solution was maintained at 0° C. for 4 hours, then warmed to 25° C. for 4 hours. The reaction mixture was diluted with ethyl acetate (200 mL) and washed with water (1×200 mL), 1N HCl (1×100 mL), dried with magnesium sulfate and concentrated to a yellow solid (455 mg, 65% yield). The product thus produced was enamide 13 wherein $R^2$ is methyl and $R^4$ is tert-butyl. $^1$H NMR (CDCl$_3$,300 MHz) δ6.11 (bs, 1H), 6.02–5.99 (d, J=10.8 Hz, 1H), 3.75 (s, 3H), 1.76–1.66 (m, 1H), 1.04–0.98 (m, 2H), 0.68–0.63 (m, 2H); $^{13}$C NMR (CDCl$_3$,75 MHz) δ165.2, 142.9, 80.2, 52.0, 44.4, 28.1, 14.1, 11.5, 8.6.

Example 5

A 100 mL flask was charged with the enamide (2.0 g, 6.2 mmol) from Example 3, DMAP (0.2 eq, 151 mg) and anhydrous THF (0.3 M, 21 mL) under an inert atmosphere. Di-tert-butyl dicarbonate (3 eq, 4 g) was added to the solution at 25° C. and the reaction mixture was stirred at 25° C. overnight (15 hours). The solution was diluted with methanol (5 mL) and cooled to 0° C. in an ice bath. 55% Aqueous hydrazine hydrate (4 eq, 0.8 mL) was added slowly over 1 minute. The solution was kept at 0° C. for 4 hours. The reaction mixture was diluted with ethyl acetate (100 mL) and washed with water (2×100 mL). The organic layer was then washed with 0.5 N HCl (1×100 mL), saturated NaHCO$_3$ (1×50 mL), dried over Na$_2$SO$_4$ and concentrated to a white solid (1.63 g, 83% yield). The product thus produced was enamide 13 wherein $R^2$ is benzyl and $R^4$ is tert-butyl. $^1$H NMR (CDCl$_3$,300 MHz) δ7.37–7.26 (m, 5H), 6.07–6.04 (d, J=10.8 Hz, 1H), 5.92 (bs, 1H), 5.18 (s, 2H), 1.76–1.66 (m, 1H), 1.45 (s, 9H), 1.03–0.97 (s, 2H), 0.66–0.63 (m, 2H); $^{13}$C NMR (CDCl$_3$,75 MHz) δ177.0; 164.6; 143.4; 128.4; 128.2; 128.1; 110.7; 80.2; 68.6; 66.8; 28.1; 11.6; 8.7

Example 6

Phosphonate ester 19a ($R^1$=t-butyloxy, $R^2$=$R^{16}$=Me)(1.0 g; 3.37 mmol) was dissolved in 5 mL of THF and cooled in ice-water. Tetramethylguanidine (0.50 mL; 4.1 mmol; 1.2 equiv) was added and the reaction mixture was stirred for 15 minutes. CPCA (0.31 mL; 4.1 mmol; 1.2 equiv) was added and the reaction mixture was allowed to warm to ambient temperature and stirred overnight. The mixture was diluted with ethyl acetate and washed sequentially with water (10 mL), 0.3 M HCl (30 mL), and saturated aqueous sodium bicarbonate (10 mL). The organic solution was dried with magnesium sulfate and concentrated to afford 0.84 g (99%) of enamide 6 wherein $R^1$ is t-butyloxy and $R^2$ is methyl. Analytical details are as presented in Example 4.

Example 7

Phosphonate ester 19b ($R^1$=$R^2$=$R^{16}$=Me)(2.39 g; 10.0 mmol) was slurried in 10 mL of ethyl acetate and cooled in ice-water. Tetramethylguanidine (1.51 mL; 12 mmol; 1.2 equiv) was added and the reaction mixture was stirred for 15 minutes. CPCA (0.90 mL; 12 mmol; 1.2 equiv) was added and the reaction mixture was allowed to warm to ambient temperature and stirred overnight. The mixture was diluted with 1.5 N HCl (20 mL) and the layers were separated. The aqueous layer was extracted with two 20-mL portions of ethyl acetate. The combined organic solution was dried with magnesium sulfate and concentrated to afford 2.35 g of crude product. This material was recrystallized from hot ethyl acetate by the addition of heptane and cooling to 0° C. to afford 1.55 g (85%) of enamide 6 wherein $R^1$ and $R^2$ are methyl. $^1$H NMR (CDCl$_3$,300 MHz) E isomer: δ6.92 (br s,1H); 6.133 (d, J=10.71 Hz, 1H); 3.729 (s, 3H); 2.131 (s, 3H); 1.59 (m, 1H); 1.02 (m, 2H); 0.68 (m, 2H); Z isomer: δ6.85 (br s,1H); 6.3 (d,1H); 3.355 (s, 3H); 1.958 (s, 3H); 1.75 (m, 1H); 1.05 (m, 2H); 0.73 (m, 2H).

Example 8

A Fischer-Porter tube was charged with the enamide (400 mg, 1.7 mmol) from Example 2 and anhydrous methanol (4.0 mL) under an argon atmosphere. Argon was bubbled through the solution for 20 minutes before the addition of commercially available (S,S)-1,2-bis-(2,5-diethylphospholano)benzene-rhodium complex (Ethyl-DuPHOS-Rh, ~2 mg, 0.6 mol %). The vessel was sealed and pressurized to 3.4 barg (approximately 50 psig) with hydrogen. After 18 hours at ambient temperature, the mixture was diluted with hexane (4.0 mL) and filtered through silica gel to remove the catalyst. The product was isolated as a white solid (99% yield, 98.9% ee). The product, having formula 5 wherein $R^1$ is phenyl and $R^2$ is methyl, was recrystallized from aqueous methanol to provide white needles (99.7% ee). Chiral GC [CP-Chirosil Val (Varian) 175° C. isothermal, 20 psig He column pressure]: $t_R$=22.90 min (minor), $t_R$=23.63 min (major). $^1$H NMR (CDCl$_3$, 300 MHz) δ7.80–7.76 (m, 2H), 7.50–7.36 (m, 3H), 4.62–4.57 (m, 1H), 3.66 (s, 3H), 1.81–1.75 (m, 1H), 1.69–1.63 (m, 1H), 0.80–0.75 (m, 1H), 0.45–0.39 (m, 2H), 0.09–0.04 (m, 2H); $^{13}$C NMR (CDCl$_3$, 75 MHz) δ133.0, 129.7, 128.7, 55.3, 52.9, 37.5, 23.6, 9.1, 5.4, 4.8.

Example 9

A Fischer-Porter tube was charged with the enamide (500 mg, 2.1 mmol) from Example 2 and anhydrous methanol (4.0 mL) under an argon atmosphere. Argon was bubbled through the solution for 20 minutes before the addition of (R,R)-Ethyl-DuPHOS-Rh (~2 mg, 0.5 mol %). The vessel was sealed and pressurized to 3.4 barg (approximately 50 psig) with hydrogen. After 18 hours at ambient temperature, the mixture was diluted with hexane (4.0 mL) and filtered through silica gel to remove the catalyst. The product, having formula 4 wherein $R^1$ is phenyl and $R^2$ is methyl, was isolated as a white solid (99% yield, 96% ee). The product was recrystallized from aqueous methanol to provide white needles (99.2% ee). Chiral GC [CP-Chirosil Val (Varian) 175° C. isothermal, 20 psig He column pressure]: $t_R$=22.97 min (major), $t_R$=23.74 min (minor). $^1$H NMR (CDCl$_3$, 300 MHz) δ7.80–7.76 (m, 2H), 7.50–7.36 (m, 3H), 4.62–4.57 (m, 1H), 3.66 (s, 3H), 1.81–1.75 (m, 1H), 1.69–1.63 (m, 1H), 0.80–0.75 (m, 1H), 0.45–0.39 (m, 2H), 0.09–0.04 (m, 2H); $^{13}$C NMR (CDCl$_3$, 75 MHz) δ133.0, 129.7, 128.7, 55.3, 52.9, 37.5, 23.6, 9.1, 5.4, 4.8.

Example 10

A Fischer-Porter tube was charged with the enamide (100 mg, 0.31 mmol) from Example 3 and anhydrous methanol (4.0 mL) under an argon atmosphere. Argon was bubbled through the solution for 20 minutes before the addition of (R,R)-Ethyl-DuPHOS-Rh (~2 mg, 2 mol %). The vessel was sealed and pressurized to 2.8 barg (approximately 40 psig) with hydrogen. After 20 hours at ambient temperature, the mixture was diluted with hexane (4.0 mL) and filtered through silica gel to remove the catalyst. The product, having formula 4 wherein $R^1$ is phenyl and $R^2$ is benzyl, was isolated as a white solid (99% yield, 72% ee). Chiral GC [CP-Chirosil Val (Varian) 175° C. isothermal, 1.4 barg (20 psig) He column pressure]: $t_R$=26.93 min (major), $t_R$=27.73 min (minor). $^1$H NMR (CDCl$_3$, 300 MHz) δ7.81–7.77 (m, 2H), 7.49–7.40 (m, 8H), 7.10–7.08 (d, J=7.5 Hz, 1H), 5.18 (s, 2H), 4.92–4.85 (m, 1H), 1.83–1.76 (m, 2H), 0.85–0.68 (m,1H), 0.48–0.41 (m, 2H), 0.09–0.03 (m, 2H).

Example 11

A Fischer-Porter tube was charged with the enamide (200 mg, 0.63 mmol) from Example 3 and anhydrous THF (4.0 mL) under an argon atmosphere. Argon was bubbled through the solution for 20 minutes before the addition of (S,S)-Ethyl-DuPHOS-Rh (~2 mg, 1 mol %). The vessel was sealed and pressurized to 3.4 barg (approximately 50 psig) with hydrogen. After 5 days at ambient temperature, the mixture was diluted with hexane (4.0 mL) and filtered through silica gel to remove the catalyst. The product, having formula 5 wherein $R^1$ is phenyl and $R^2$ is benzyl, was isolated as a white solid (99% yield, 66% ee). Chiral GC [CP-Chirosil Val (Varian) 175° C. isothermal, 1.4 barg (20 psig) He column pressure]: $t_R$=26.58 min (minor), $t_R$=28.00 min (major). $^1$H NMR (CDCl$_3$, 300 MHz) δ7.81–7.77 (m, 2H), 7.49–7.40 (m, 8H), 7.10–7.08 (d, J=7.5 Hz, 1H), 5.18 (s, 2H), 4.92–4.85 (m, 1H), 1.83–1.76 (m, 2H), 0.85–0.68 (m, 1H), 0.48–0.41 (m, 2H), 0.09–0.03 (m, 2H).

Example 12

A Fischer-Porter tube was charged with the enamide (150 mg, 0.77 mmol) from Example 4 and anhydrous THF (4.0 mL) under an argon atmosphere. Argon was bubbled through the solution for 20 minutes before the addition of (S,S)-Ethyl-DuPHOS-Rh (~2 mg, 1 mol %). The vessel was sealed and pressurized to 2.8 barg (approximately 40 psig) with hydrogen. After 18 hours at ambient temperature, the mixture was diluted with hexane (4.0 mL) and filtered through silica gel to remove the catalyst. The product, having formula 5 wherein $R^1$ is tert-butoxy and $R^2$ is methyl, was isolated as a white solid (99% yield, 99.7% ee). Chiral GC [CP-Chirosil Val (Varian) 175° C. isothermal, 1.03 barg (15 psig) He column pressure]: $t_R$=14.59 min (major), $t_R$=15.21 min (minor). $^1$H NMR (CDCl$_3$, 300 MHz) δ5.22–5.20 (m, 1H), 4.41–4.34 (m, 1H), 3.74 (s, 3H), 1.69–1.64 (t, J=6.6 Hz, 2H), 0.73–0.67 (m, 1H), 0.51–0.44 (m, 2H), 0.10–0.05 (m, 2H).

Example 13

A Fischer-Porter tube was charged with the enamide (100 mg, 0.32 mmol) from Example 5 and anhydrous THF (4.0 mL) under an argon atmosphere. Argon was bubbled through the solution for 20 minutes before the addition of (S,S)-Ethyl-DuPHOS-Rh (~2 mg, 1 mol %). The vessel was sealed and pressurized to 2.8 barg (approximately 40 psig) with hydrogen. After 18 hours at ambient temperature, the mixture was diluted with hexane (4.0 mL) and filtered through silica gel to remove the catalyst. The product, having formula 5 wherein $R^1$ is tert-butoxy and $R^2$ is benzyl, was isolated as a white solid (99% yield, 99.3% ee). Chiral GC [CP-Chirosil Val (Varian) 175° C. isothermal, 1.03 barg (15 psig) He column pressure]: $t_R$=15.23 min (minor), $t_R$=15.89 min (major). $^1$H NMR (CDCl$_3$, 300 MHz) δ7.41–4.30 (m, 5H), 5.13–5.12 (m, 1H), 5.02 (s, 2H), 1.70–1.60 (m, 2H), 1.45 (s, 9H), 0.69–0.61 (m, 1H), 0.42–0.39 (m, 2H), 0.02–0.01 (m, 2H).

Example 14

A Fischer-Porter tube was charged with (R)-N-methyl-N-diphenyl-phosphino-1-[(S)-2-(diphenylphosphino)ferrocenyl]ethylamine (14a, $R^5$=$R^6$=methyl, $R^7$=R8=phenyl, n=m=0, $M^2$=iron)(22 mg, 11 mol %) and anhydrous THF (4.0 mL) under an argon atmosphere. Argon was bubbled through the solution for 20 minutes before the addition of bis(1,5-cyclooctadienyl)rhodium trifluoromethanesulfonate (8.3 mol %, 12 mg). The solution stirred at 25° C. for 5 minutes or until all of the rhodium salt had dissolved. The enamide (100 mg, 0.32 mmol) from Example 5 was added. The vessel was sealed and pressurized to 2.8 barg (approximately 40 psig) with hydrogen. After 18 hours at ambient temperature, the mixture was diluted with hexane (4.0 mL) and filtered through silica gel to remove the catalyst. The product, having formula 5 wherein $R^1$ is tert-butoxy and $R^2$ is benzyl, was isolated as a white solid (99% yield, 98.6% ee). Chiral GC [CP-Chirosil Val (Varian) 175° C. isothermal, 1.03 barg (15 psig) He column pressure]: $t_R$=15.23 (minor), $t_R$=15.89 (major). $^1$H NMR (CDCl$_3$) δ7.41–4.30 (m, 5H), 5.13–5.12 (m, 1H), 5.02 (s, 2H), 1.70–1.60 (m, 2H), 1.45 (s, 9H), 0.69–0.61 (m, 1H), 0.42–0.39 (m, 2H), 0.02–0.01 (m, 2H).

Example 15

Bis(1,5-cyclooctadiene)rhodium trifluoromethanesulfonate (2.3 mg; 5 μmol; 0.01 equiv) was placed into a reaction vessel and purged with argon for 15 min. A solution of 14a (3.7 mg; 6 μmol; 0.012 equiv) in anhydrous THF (2.0 mL) was degassed with Ar for 15 minutes, then added via cannula to the bis(1,5-cyclooctadiene)rhodium trifluoromethanesulfonate. This solution was stirred at 25° C. under argon for 15 minutes. A solution of enamide 6 from Example 2 (123 mg; 0.5 mmol) in anhydrous THF (2.0 mL) was degassed with argon for 20 minutes, then added to the catalyst solution via cannula. The solution was then flushed with hydrogen and pressurized to 0.69–1.38 bars gauge (10–20 pounds per square inch gauge—psig) hydrogen and agitated at ambient temperature for 24 h to afford 100% conversion to the product having formula 5 wherein $R^1$ is phenyl and $R^2$ is methyl with 91.6% ee as determined by chiral GC. See Example 8 for analytical details.

Example 16

Bis(1,5-cyclooctadiene)rhodium trifluoromethanesulfonate (2.3 mg; 5 μmol; 0.01 equiv ) was placed into a reaction vessel and purged with argon for 15 min. A solution of 14a (3.7 mg; 6 μmol; 0.012 equiv) in anhydrous THF (2.0 mL) was degassed with Ar for 15 minutes, then added via cannula to the bis(1,5-cyclooctadiene)rhodium trifluoromethanesulfonate. This solution was stirred at 25° C. under argon for 15 minutes. A solution of enamide 13 from Example 4 (121 mg; 0.5 mmol) in anhydrous THF (2.0 mL) was degassed with argon for 20 minutes, then added to the catalyst solution via cannula. The solution was then flushed with hydrogen and pressurized to 0.69–1.38 bars gauge (10–20 pounds per square inch gauge—psig) hydrogen and agitated at ambient temperature for 6 h to afford 90% conversion to the product having formula 5 wherein $R^1$ is t-butoxy and $R^2$ is methyl with 98.6% ee as determined by chiral GC. See Example 12 for analytical details.

Example 17

Bis(1,5-cyclooctadiene)rhodium trifluoromethanesulfonate (2.3 mg; 5 μmol; 0.01 equiv ) was placed into a reaction vessel and purged with argon for 15 min. A solution of 14a (3.7 mg; 6 μmol; 0.012 equiv) in anhydrous THF (3.0 mL) was degassed with Ar for 15 minutes, then added via cannula to the bis(1,5-cyclooctadiene)rhodium trifluoromethanesulfonate. This solution was stirred at 25° C. under argon for 15 minutes. A solution of enamide 6 from Example 7 (92 mg; 0.5 mmol) in anhydrous THF (3.0 mL) was degassed with argon for 20 minutes, then added to the catalyst solution via cannula. The solution was then flushed with hydrogen and pressurized to 0.69–1.38 bars gauge (10–20 pounds per square inch gauge—psig) hydrogen and agitated at ambient temperature for 1 h to afford 100% conversion to the product having formula 5 wherein both $R^1$ and $R^2$ are methyl with 96.4% ee as determined by chiral GC. $^1$H NMR (CDCl$_3$,300 MHz) δ6.20 (br s, 1H); 4.66 (m, 1H); 3.733 (s, 3H); 2.019 (s, 3H); 1.731 (dd, J=6.04, 14.01 Hz, 1H); 1.635 (dd, J=6.41, 14.01 Hz, 1H); 0.66 (m, 1H); 0.45 (m, 2H); 0.048 (m, 2H). Chiral GC [CP-Chirosil Val (Varian) 125° C. isothermal, 1.03 barg (15 psig) He column pressure]: $t_R$=8.25 min (minor), $t_R$=9.30 min (major).

Example 18

(S,S)-Ethyl-DuPHOS-Rh (3.6 mg; 5 μmol; 0.01 equiv) was placed into a reaction vessel and purged with argon for 15 min. Degassed anhydrous THF (3.0 mL) was via cannula. This solution was stirred at 25° C. under argon for 15 minutes. A solution of enamide 6 from Example 7 (92 mg; 0.5 mmol) in anhydrous THF (3.0 mL) was degassed with argon for 15 minutes, then added to the catalyst solution via cannula. The solution was then flushed with hydrogen and pressurized to 0.69–1.38 bars gauge (10–20 psig) hydrogen and agitated at ambient temperature for 1 h to afford 100% conversion to the product having formula 5 wherein both $R^1$ and $R^2$ are methyl with 99.6% ee as determined by chiral GC.

Example 19

Bis(1,5-cyclooctadiene)rhodium trifluoromethanesulfonate (2.3 mg; 5 μmol; 0.01 equiv) and 14a (3.7 mg; 6 μmol; 0.012 equiv) were placed in a high pressure reaction vessel which was sealed and purged with argon. Degassed acetone (2 mL) was added the the resulting solution was stirred at 25° C. under argon for 15 minutes. A solution of enamide 13 from Example 5 (153 mg; 0.5 mmol) in acetone (2.0 mL) was added via syringe and washed in with 1.0 mL of acetone. The solution was then purged five times with argon and pressurized with hydrogen to 20.7 barg (300 psig) and stirred at ambient temperature for 6 h. The reaction vessel was vented and purged with argon. A sample was removed and analyzed by chiral GC to indicate 100% conversion to the product having formula 5 wherein $R^1$ is t-butoxy and $R^2$ is benzyl with 96.6% ee. See Example 13 for analytical details.

The invention has been described in detail with particular reference to preferred embodiments thereof, but it will be understood that variations and modifications can be effected within the spirit and scope of the invention.

We claim:

1. A process for the preparation of an enantiomerically-enriched cyclopropylalanine compound having the formula

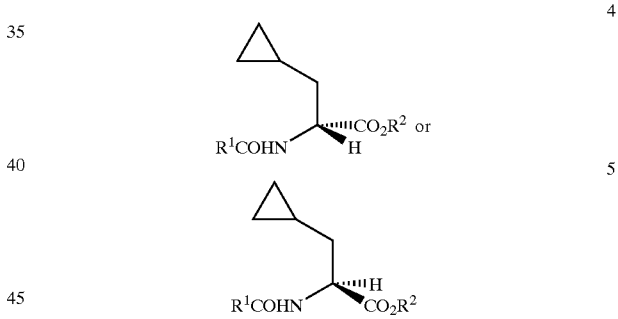

which comprises contacting an enamide having the formula

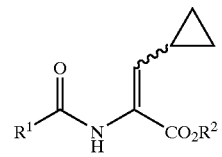

with hydrogen in the presence of a catalyst system comprising a transition metal and a substantially enantiomerically-pure bis-phosphine under hydrogenation conditions of pressure and temperature; wherein $R^1$ is hydrogen, substituted or unsubstituted $C_1$ to $C_{20}$ alkyl, substituted or unsubstituted $C_1$ to $C_{20}$ alkoxy, substituted or unsubstituted $C_3$ to $C_8$ cycloalkyl, substituted or unsubstituted $C_3$ to $C_8$ cycloalkoxy, substituted or unsubstituted carbocyclic $C_6$ to $C_{20}$ aryl, substituted or unsubstituted carbocyclic $C_6$ to $C_{20}$ aryloxy, substituted or unsubstituted $C_4$ to $C_{20}$ heteroaryl wherein the heteroatoms are selected from sulfur, nitrogen, and oxygen or substituted or unsubstituted $C_4$ to $C_{20}$ heteroaryloxy wherein the heteroatoms are selected from sulfur, nitrogen, and oxygen; $R^2$ is hydrogen, unsubstituted or substituted $C_1$ to $C_{20}$ alkyl, substituted or unsubstituted $C_3$ to $C_8$ cycloalkyl, unsubstituted or substituted carbocyclic $C_6$ to $C_{20}$ aryl, or substituted or unsubstituted $C_4$ to $C_{20}$ heteroaryl wherein the heteroatoms are selected from sulfur, nitrogen, and oxygen; and the bis-phosphine has the formula

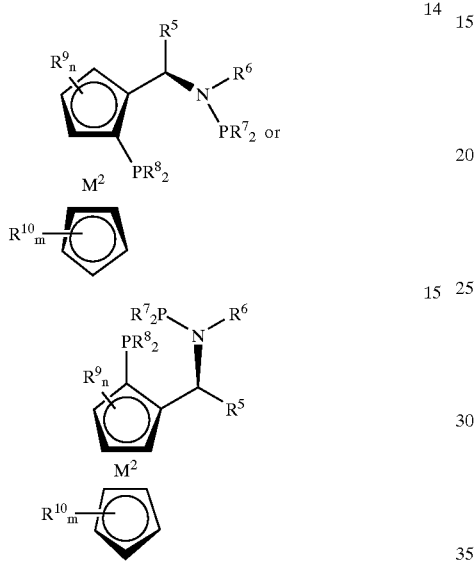

wherein $R^5$ is selected from substituted and unsubstituted, branched- and straight-chain $C_1$ to $C_{20}$ alkyl, substituted and unsubstituted $C_3$ to $C_8$ cycloalkyl, substituted and unsubstituted $C_6$ to $C_{20}$ carbocyclic aryl, and substituted and unsubstituted $C_4$ to $C_{20}$ heteroaryl wherein the heteroatoms are selected from sulfur, nitrogen, and oxygen;

$R^6$, $R^7$, $R^8$, $R^9$, and $R^{10}$ are independently selected from hydrogen, substituted and unsubstituted, branched- and straight-chain $C_1$ to $C_{20}$ alkyl, substituted and unsubstituted $C_3$ to $C_8$ cycloalkyl, substituted and unsubstituted $C_6$ to $C_{20}$ carbocyclic aryl, and substituted and unsubstituted $C_4$ to $C_{20}$ heteroaryl wherein the heteroatoms are selected from sulfur, nitrogen, and oxygen;

n is 0 to 3;

m is 0 to 5; and $M^2$ is selected from the metals of Groups IVB, VB, VIB, VIIB and VIII.

2. A process according to claim 1 wherein the transition metal is ruthenium, rhodium or iridium; and the hydrogenation conditions of pressure and temperature comprise a hydrogen pressure of about 0.5 to 69 bars gauge and a temperature in the range of about −20 to 100° C.

3. A process according to claim 2 wherein the hydrogenation conditions of pressure and temperature comprise a hydrogen pressure of about 0.69 to 20.7 bars gauge and a temperature of about 0 to 50° C.; $R^1$ is $C_1$ to $C_6$ alkyl, phenyl, tolyl, or $C_1$ to $C_6$ alkoxy; and $R^2$ is $C_1$ to $C_6$ alkyl or benzyl.

4. A process for the preparation of an enantiomerically-enriched cyclopropylalanine compound having formula 4 or 5

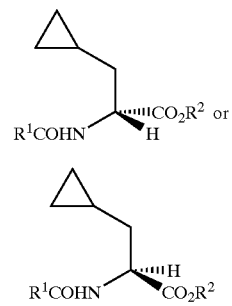

by the steps comprising (1) contacting cyclopropanecarboxaldehyde (CPCA) with an N-acylglycine having the formula

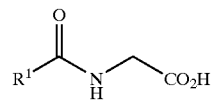

in the presence of a carboxylic acid anhydride and a base at elevated temperature to produce an azlactone having the formula

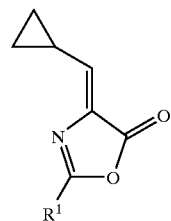

(2) contacting azlactone 8 with an alcohol to produce an enamide having the formula

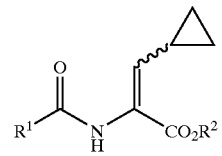

and (3) contacting enamide 6 with hydrogen in the presence of a catalyst system comprising a transition metal and a substantially enantiomerically-pure bis-phosphine under hydrogenation conditions of pressure and temperature; wherein $R^1$ is hydrogen, substituted or unsubstituted $C_1$ to $C_{20}$ alkyl, substituted or unsubstituted $C_1$ to $C_{20}$ alkoxy, substituted or unsubstituted $C_3$ to $C_8$ cycloalkyl, substituted or unsubstituted $C_3$ to $C_8$ cycloalkoxy, substituted or unsubstituted carbocyclic $C_6$ to $C_{20}$ aryl, substituted or unsubstituted carbocyclic $C_6$ to $C_{20}$ aryloxy, substituted or unsubstituted $C_4$ to $C_{20}$ heteroaryl wherein the heteroatoms are selected from sulfur, nitrogen, and oxygen or substituted or unsubstituted C$_4$ to C$_{20}$ heteroaryloxy wherein the heteroatoms are selected from sulfur, nitrogen, and oxygen; and R$^2$ is hydrogen, substituted or unsubstituted C$_1$ to C$_{20}$ alkyl, substituted or unsubstituted C$_3$ to C$_8$ cycloalkyl, substituted or unsubstituted carbocyclic C$_6$ to C$_{20}$ aryl, or C$_4$ to C$_{20}$ heteroaryl wherein the heteroatoms are selected from sulfur, nitrogen, and oxygen.

5. A process according to claim 4 wherein step (1) is carried out at a temperature of about 35 to 150° C. in the presence of acetic anhydride and a base selected from the acetates, carbonates and bicarbonates of lithium, sodium, potassium, cesium, magnesium, calcium, lead and barium; step (2) is carried out at a temperature of about −10 to 100° C. in the presence of an alcohol and an alkali or alkaline earth metal alkoxide or hydroxide; and step (3) is carried out in the presence of a transition metal selected from ruthenium, rhodium or iridium; and a substantially enantiomerically-pure bis-phosphine selected from 2,3-O-isopropylidene-2,3-dihydroxy-1,4-2,3-bis-(diphenylphosphino)butane, 2,2'-bis(diphenylphosphino)-1,1'-binaphthyl, 1,2-bis-2,5-dialkylpholano(benzene), 1,2-bis-2,5-dialkylphospholano(ethane), 2,3-bis-(diphenylphosphino)butane, 2-diphenylphosphinomethyl-4-diphenylphosphino-1-t-butoxycarbonylpyrrolidine and bis-phosphine compounds comprising a substantially enantiomerically pure chiral backbone linking two phosphine residues wherein one of the phosphine residues has three phosphorus-carbon bonds and the other phosphine residue has two phophorus-carbon bonds and one phosphorus-nitrogen bond wherein the nitrogen is part of the chiral backbone; under hydrogenation conditions of pressure and temperature comprising a hydrogen pressure of about 0.5 to 69 bars gauge and a temperature in the range of about −20 to 100° C.

6. A process according to claim 4 wherein step (1) is carried out at a temperature of about 85 to 110° C. in the presence of acetic anhydride arid sodium acetate; step (2) is carried out at a temperature of about 25 to 50° C. in the presence of an alcohol and an alkali metal alkoxide or hydroxide selected from the alkoxides and hydroxides of sodium and potassium; and step (3) is carried out in the presence of a catalyst system comprising a transition metal selected from ruthenium or rhodium and a substantially enantiomerically-pure 1,2-bis-(2,5-dialkylpholano) benzene wherein each alkyl group contains 1 to 6 carbon atoms or a substantially enantiomerically-pure bis-phosphine having the formula

14

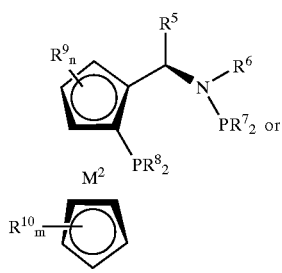

-continued

15

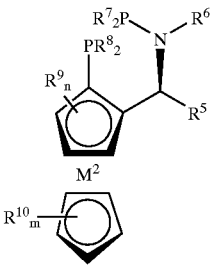

wherein

R$^5$ is selected from substituted and unsubstituted, branched- and straight-chain C$_1$ to C$_{20}$ alkyl, substituted and unsubstituted C$_3$ to C$_8$ cycloalkyl, substituted and unsubstituted C$_6$ to C$_{20}$ carbocyclic aryl, and substituted and unsubstituted C$_4$ to C$_{20}$ heteroaryl wherein the heteroatoms are selected from sulfur, nitrogen, and oxygen;

R$^6$, R$^7$, R$^8$, R$^9$, and R$^{10}$ are independently selected from hydrogen, substituted and unsubstituted, branched- and straight-chain C$_1$ to C$_{20}$ alkyl, substituted and unsubstituted C$_3$ to C$_8$ cycloalkyl, substituted and unsubstituted C$_6$ to C$_{20}$ carbocyclic aryl, and substituted and unsubstituted C$_4$ to C$_{20}$ heteroaryl wherein the heteroatoms are selected from sulfur, nitrogen, and oxygen;

n is 0 to 3;

m is 0 to 5; and

M$^2$ is selected from the metals of Groups IVB, VB, VIB, VIIB and VIII; under hydrogenation conditions of pressure and temperature comprising a hydrogen pressure of about 0.5 to 69 bars gauge and a temperature in the range of about −20 to 100° C.

7. A process according to claim 6 wherein, in step (3), the transition metal is ruthenium or rhodium; the bis-phosphine is a substantially enantiomerically-pure N-alkyl-N-diphenylphosphino-1-[2-(diphenylphosphino)ferrocenyl] alkylamine wherein each alkyl group independently contains 1 to 6 carbon atoms or 1,2-bis-(2,5-dialkylphospholano)benzene (DuPHOS) wherein each alkyl group contains 1 to 6 carbon atoms; the hydrogenation conditions of pressure and temperature comprise a hydrogen pressure of about 0.69 to 20.7 bars gauge and a temperature of about 0 to 50° C.; R$^1$ is C$_1$ to C$_6$ alkyl, phenyl, tolyl, or C$_1$ to C$_6$ alkoxy; and R$^2$ is C$_1$ to C$_6$ alkyl or benzyl.

8. A process according to claim 6 wherein in Step (1) the base is sodium acetate; step (2) is carried out in the presence of benzyl alcohol and sodium methoxide; and step (3) is carried out in the presence of a catalyst system comprising a transition metal selected from ruthenium or rhodium and a substantially enantiomerically-pure N-alkyl-N-diphenylphosphino-1-[2-(diphenylphosphino)ferrocenyl] ethylamine wherein the alkyl group contains 1 to 6 carbon atoms or 1,2-bis-(2,5-dialkylphospholano)benzene (DuPHOS) wherein each alkyl group contains 1 to 6 carbon atoms; the hydrogenation conditions of pressure and temperature comprise a hydrogen pressure of about 0.69 to 20.7 bars gauge and a temperature of about 0 to 50° C.; R$^1$ is methyl; and R$^2$ is benzyl.

9. A process for the preparation of an enantiomerically-enriched cyclopropylalanine compound having the formula

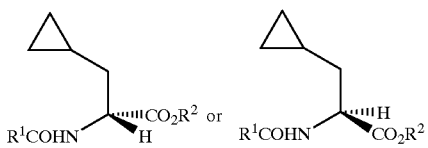  5 by the steps comprising (i) contacting cyclopropanecarboxaldehyde (CPCA) with an N-acylglycine having the formula

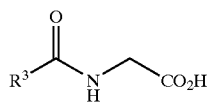  9 in the presence of a carboxylic acid anhydride and a base at elevated temperature to produce an azlactone having the formula

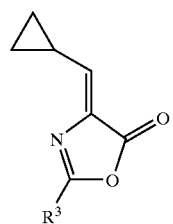  10

(ii) contacting azlactone 10 with an alcohol to produce an enamide having the formula

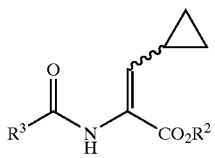  11

(iii) contacting enamide 11 with an acylating agent having the formula $R^4O-C(O)-O-C(O)-OR^4$ or $R^4O-C(O)-X$ wherein X is fluorine, chlorine, bromine, or iodine in the presence of 4-(N,N-dimethylamino)pyridine (DMAP) and an inert organic solvent to produce an amido-carbamate having formula 12

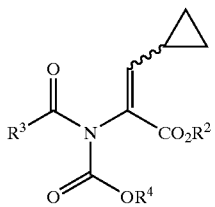  12

(iv) contacting amido-carbamate 12 with a nucleophile in the presence of an inert organic solvent to produce a second enamide having formula 13

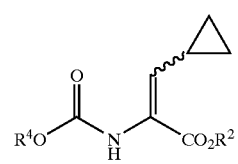  13 and (iv) contacting enamide 13 with hydrogen in the presence of a catalyst system comprising a transition metal and a substantially enantiomerically-pure bis-phosphine under hydrogenation conditions of pressure and temperature; wherein $R^2$ is hydrogen, substituted or unsubstituted $C_1$ to $C_{20}$ alkyl, substituted or unsubstituted $C_3$ to $C_8$ cycloalkyl, substituted or unsubstituted carbocyclic $C_6$ to $C_{20}$ aryl, or substituted or unsubstituted $C_4$ to $C_{20}$ heteroaryl wherein the heteroatoms are selected from sulfur, nitrogen, or oxygen; and $R^3$ and $R^4$ are independently selected from substituted and unsubstituted $C_1$ to $C_{20}$ alkyl, substituted and unsubstituted $C_3$ to $C_8$ cycloalkyl, substituted and unsubstituted carbocyclic $C_6$ to $C_{20}$ aryl, $C_4$ to $C_{20}$ heteroaryl wherein the heteroatoms are selected from sulfur, nitrogen, and oxygen.

10. A process according to claim 9 wherein step (i) is carried out at a temperature of about 35 to 150° C. in the presence of acetic anhydride and a base selected from the acetates, carbonates and bicarbonates of lithium, sodium, potassium, cesium, magnesium, calcium, lead and barium; step (ii) is carried out at a temperature of about −10 to 100° C. in the presence of an alcohol and an alkali or alkaline earth metal alkoxide or hydroxide; step (iii) is carried out in the presence of di-tert-butyl dicarbonate as the acylating agent and at a temperature of about −20 to 45° C.; step (iv) is carried out in the presence of an alkanol solvent and a nucleophile selected from hydrazine and hydrazine hydrate at a temperature of about −40 to 15° C.; and step (v) is carried out in the presence of a catalyst system comprising a transition metal selected from ruthenium, rhodium or iridium and a substantially enantiomerically-pure bis-phosphine selected from 2,3-O-isopropylidene-2,3-dihydroxy-1,4-bis(diphenylphosphino)butane, 2,2'-bis(diphenylphosphino)-1,1'-binaphthyl, 1,2-bis-(2,5-dialkylphospholano)benzene, 1,2-bis-2,5-dialkylphospholano(ethane), 2,3-bis(diphenylphosphino)butane, 2-diphenylphosphinomethyl-4-diphenylphosphino-1-t-butoxycarbonylpyrrolidine and bis-phosphine compounds comprising a substantially enantiomerically pure chiral backbone linking two phosphine residues wherein one of the phosphine residues has three phosphorus-carbon bonds and the other phosphine residue has two phophorus-carbon bonds and one phosphorus-nitrogen bond wherein the nitrogen is part of the chiral backbone; under hydrogenation conditions of pressure and temperature comprising a hydrogen pressure of about 0.5 to 69 bars gauge and a temperature in the range of about −20 to 100° C.

11. A process according to claim 9 wherein step (i) is carried out at a temperature of about 85 to 110° C. in the presence of acetic anhydride arid sodium acetate; step (ii) is carried out at a temperature of about 25 to 50° C. in the presence of an alcohol and an alkali metal alkoxide or hydroxide selected from the alkoxides and hydroxides of sodium and potassium; step (iii) is carried out in the presence of an inert, organic solvent and di-tert-butyl dicarbonate as the acylating agent and at a temperature of about 15 to 35° C.; step (iv) is carried out in the presence of an alkanol solvent selected from methanol and ethanol and a nucleophile selected from hydrazine and hydrazine hydrate at a temperature of about −5 to 5° C.; and step (v) is carried out in the presence of a catalyst system comprising a transition metal selected from ruthenium and rhodium and a substantially enantiomerically-pure 1,2-bis-(2,5-dialkylphospholano) benzene wherein each alkyl group contains 1 or 6 carbon atoms or a substantially enantiomerically-pure bis-phosphine having the formula

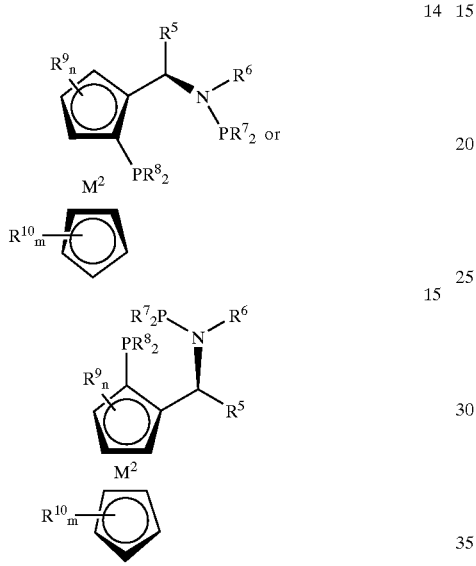

wherein
R⁵ is selected from substituted and unsubstituted, branched- and straight-chain $C_1$ to $C_{20}$ alkyl, substituted and unsubstituted $C_3$ to $C_8$ cycloalkyl, substituted and unsubstituted $C_6$ to $C_{20}$ carbocyclic aryl, and substituted and unsubstituted $C_4$ to $C_{20}$ heteroaryl wherein the heteroatoms are selected from sulfur, nitrogen, and oxygen;
R⁶, R⁷, R⁸, R⁹, and R¹⁰ are independently selected from, substituted and unsubstituted, branched- and straight-chain $C_1$ to $C_{20}$ alkyl, substituted and unsubstituted $C_3$ to $C_8$ cycloalkyl, substituted and unsubstituted $C_5$ to $C_{20}$ carbocyclic aryl, and substituted and unsubstituted $C_4$ to $C_{20}$ heteroaryl wherein the heteroatoms are selected from sulfur, nitrogen, and oxygen;
n is 0 to 3;
m is 0 to 5; and
M² is selected from the metals of Groups IVB, VB, VIB, VIIB and VIII; under hydrogenation conditions of pressure and temperature comprising a hydrogen pressure of about 0.5 to 69 bars gauge and a temperature in the range of about −20 to 100° C.

12. A process according to claim 11 wherein step (v) is carried out in the presence of a catalyst system comprising a transition metal selected from ruthenium and rhodium and a substantially enantiomerically-pure bis-phosphine selected from substantially enantiomerically-pure N-alkyl-N-diphenylphosphino-1-[2-(diphenylphosphino)ferrocenyl] ethylamine wherein the alkyl group contains 1 to 6 carbon atoms and 1,2-bis-(2,5-dialkylphospholano)benzene (DuPHOS) wherein each alkyl group contains 1 to 6 carbon atoms; the hydrogenation conditions of pressure and temperature comprise a hydrogen pressure of about 0.69 to 20.7 bars gauge and a temperature of about 0 to 50° C.

13. A process for the preparation of an enantiomerically-enriched cyclopropylalanine compound having formula 4 or 5

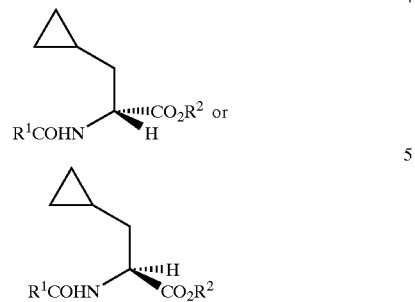

by the steps comprising
(a) contacting cyclopropanecarboxaldehyde with a phosphonate ester having the formula 19

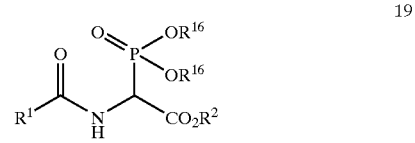

in an inert solvent in the presence of a base to form an enamide having formula 6

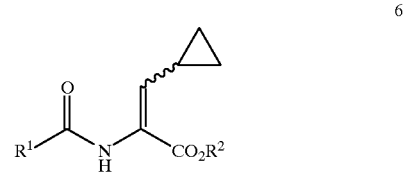

and (b) contacting enamide 6 with hydrogen in the presence of a catalyst system comprising a transition metal and a substantially enantiomerically-pure bis-phosphine under hydrogenation conditions of pressure and temperature; wherein
R¹ is hydrogen, substituted or unsubstituted $C_1$ to $C_{20}$ alkyl, substituted or unsubstituted $C_1$ to $C_{20}$ alkoxy, substituted or unsubstituted $C_3$ to $C_8$ cycloalkyl, substituted or unsubstituted $C_3$ to $C_8$ cycloalkoxy, substituted or unsubstituted carbocyclic $C_6$ to $C_{20}$ aryl, substituted or unsubstituted carbocyclic $C_6$ to $C_{20}$ aryloxy, substituted or unsubstituted $C_4$ to $C_{20}$ heteroaryl wherein the heteroatoms are selected from sulfur, nitrogen, and oxygen or substituted or unsubstituted $C_4$ to $C_{20}$ heteroaryloxy wherein the heteroatoms are selected from sulfur, nitrogen, and oxygen;
R² is hydrogen, substituted or unsubstituted $C_1$ to $C_{20}$ alkyl, substituted or unsubstituted $C_3$ to $C_8$ cycloalkyl, substituted or unsubstituted carbocyclic $C_6$ to $C_{20}$ aryl, or substituted or unsubstituted $C_4$ to $C_{20}$ heteroaryl wherein the heteroatoms are selected from sulfur, nitrogen, and oxygen;

R¹⁶ is substituted or unsubstituted $C_1$ to $C_{20}$ alkyl, substituted or unsubstituted $C_3$ to $C_8$ cycloalkyl, substituted or unsubstituted carbocyclic $C_6$ to $C_{20}$ aryl, or substituted or unsubstituted $C_4$ to $C_{20}$ heteroaryl wherein the heteroatoms are selected from sulfur, nitrogen, and oxygen; and and the bis-phosphine has the formula

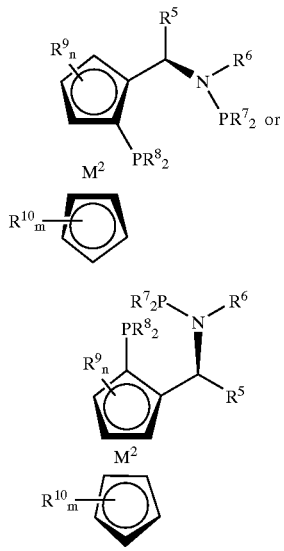

14 wherein $R^5$ is selected from substituted and unsubstituted, branched- and straight-chain $C_1$ to $C_{20}$ alkyl, substituted and unsubstituted $C_3$ to $C_8$ cycloalkyl, substituted and unsubstituted $C_6$ to $C_{20}$ carbocyclic awl, and substituted and unsubstituted $C_4$ to $C_{20}$ heteroaryl wherein the heteroatoms are selected from sulfur, nitrogen, and oxygen;

$R^6, R^7, R^8, R^9$, and $R^{10}$ are independently selected from hydrogen, substituted and unsubstituted, branched- and straight-chain $C_1$ to $C_{20}$ alkyl, substituted and unsubstituted $C_3$ to $C_8$ cycloalkyl, substituted and unsubstituted $C_6$ to $C_{20}$ carbocyclic aryl, and substituted and unsubstituted $C_4$ to $C_{20}$ heteroaryl wherein the heteroatoms are selected from sulfur, nitrogen, and oxygen;

n is 0 to 3 m is 0 to 5; and $M^2$ is selected from the metals of Groups IVB, VB, VIB, VIIB and VIII.

14. A process according to claim 13 wherein step (a) is carried out at a temperature of about −78 to 50° C. in an inert solvent selected from aliphatic hydrocarbons, cyclic and acyclic ethers, aromatic hydrocarbons, esters, and polar aprotic solvents in the presence of a base selected from alkoxides of the alkali metals and alkaline earth metals and amines; and the transition metal in step (b) is selected from ruthenium, rhodium or iridium and the hydrogenation conditions of pressure and temperature comprise a hydrogen pressure of about 0.5 to 69 bars gauge and a temperature in the range of about −20 to 100° C.

15. A process according to claim 14 wherein step (a) is carried out at a temperature of about −20 to 30° C. in the presence of tetramethylguanidine in tetrahydrofuran or ethyl acetate; and the transition metal in step (b) is selected from ruthenium and rhodium and the hydrogenation conditions of pressure and temperature comprise a hydrogen pressure of about 0.69 to 20.7 bars gauge and a temperature in the range of about 0 to 50° C.

16. A compound having the formula

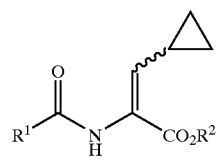

6 wherein $R^1$ is hydrogen, substituted or unsubstituted $C_1$ to $C_{20}$ alkyl, substituted or unsubstituted $C_1$ to $C_{20}$ alkoxy, substituted or unsubstituted $C_3$ to $C_8$ cycloalkoxy, substituted or unsubstituted carbocyclic $C_6$ to $C_{20}$ aryl, substituted or unsubstituted carbocyclic $C_6$ to $C_{20}$ aryloxy, substituted or unsubstituted $C_4$ to $C_{20}$ heteroaryl wherein the heteroatoms are selected from sulfur, nitrogen, and oxygen or substituted or unsubstituted $C_4$ to $C_{20}$ heteroaryloxy wherein the heteroatoms are selected from sulfur, nitrogen, and oxygen; and $R^2$ is hydrogen, unsubstituted or substituted $C_1$ to $C_{20}$ alkyl, substituted or unsubstituted $C_3$ to $C_8$ cycloalkyl, unsubstituted or substituted carboxyxlic $C_6$ to $C_{20}$ aryl, or substituted or unsubstituted $C_4$ to $C_{20}$ heteroaryl wherein the heteroatoms are selected from sulfur, nitrogen, and oxygen.

17. A compound according to claim 16 wherein $R^1$ is $C_1$ to $C_6$ alkyl, phenyl, tolyl, $C_1$ to $C_6$ alkoxy, or benzyloxy; and $R^2$ is $C_1$ to $C_6$ alkyl or benzyl.

* * * * *

UNITED STATES PATENT AND TRADEMARK OFFICE
CERTIFICATE OF CORRECTION

PATENT NO. : 6,635,784 B2  
DATED : October 21, 2003  
INVENTOR(S) : Debenham et al.

It is certified that error appears in the above-identified patent and that said Letters Patent is hereby corrected as shown below:

Column 27,  
Line 4, the listed structure

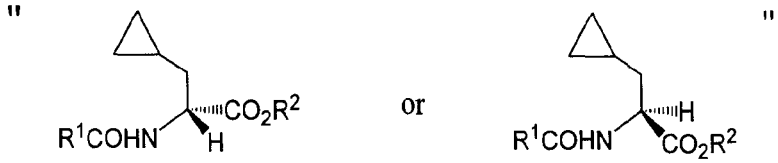

should be

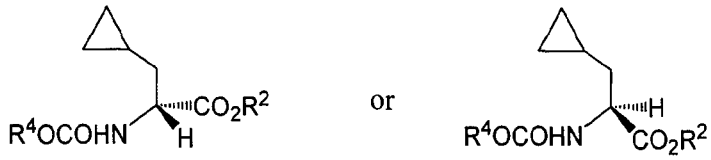

Column 29,  
Line 46, after "selected from" insert -- hydrogen --.  
Line 49, "$C_5$" should be -- $C_6$ --.

Column 31,  
Line 35, "awl," should be -- aryl, --.

Signed and Sealed this

Second Day of March, 2004

JON W. DUDAS  
*Acting Director of the United States Patent and Trademark Office*